(12) United States Patent
Paiocchi et al.

(10) Patent No.: US 7,265,251 B2
(45) Date of Patent: Sep. 4, 2007

(54) PROCESS FOR THE PREPARATION OF NITROALKENES

(75) Inventors: Maurizio Paiocchi, Milan (IT); Aldo Belli, Cornate D'Adda (IT); Francesco Ponzini, Milan (IT); Marco Villa, Padua (IT)

(73) Assignee: Zambon Group S.p.A., Vicenza (IT)

( * ) Notice: Subject to any disclaimer, the term of this patent is extended or adjusted under 35 U.S.C. 154(b) by 0 days.

(21) Appl. No.: 11/247,600

(22) Filed: Oct. 12, 2005

(65) Prior Publication Data

US 2006/0063953 A1 Mar. 23, 2006

Related U.S. Application Data

(63) Continuation of application No. 10/311,319, filed as application No. PCT/EP01/06902 on Jun. 19, 2001, now abandoned.

(30) Foreign Application Priority Data

Jun. 28, 2000 (EP) ................................. 00830453

(51) Int. Cl.
*C07C 205/00* (2006.01)
*C07C 205/05* (2006.01)
*C07D 311/22* (2006.01)

(52) U.S. Cl. ........................ 568/927; 568/929; 549/404
(58) Field of Classification Search .................... None
See application file for complete search history.

(56) References Cited

FOREIGN PATENT DOCUMENTS

WO WO98/46586 10/1998

OTHER PUBLICATIONS

D. Ghosh, et al., "An improved method for the preparation of cyclic conjugated nitroolefins", SYNTHESIS, vol. 2, pp. 195-197 (1996).
W.W. SY, et al., "Nitration of substituted styrenes with nitryl iodide", Tetrahedron Lett., vol 26, No. 9, pp. 1193-1196 (1985).
S.R. Waldman, et al., "One-Pot Claisen Rearrangement/O-Methylation/Alkene Isomerization in the Synthesis of *Ortho*-Methoxylated Phenylisopropylamines", Tetrahedron Letters, vol. 37, No. 44, pp. 7889-7892 (1996).
P.J. Campos, et al., "One-pot selective synthesis of β-nitrostyrenes from styrenes, promoted by Cu(II)", Tetrahedron Letters, vol. 41, No. 6, pp. 979-982 (2000).

*Primary Examiner*—Brian Davis
(74) *Attorney, Agent, or Firm*—Oblon, Spivak, McClelland, Maier & Neustadt, P.C.

(57) ABSTRACT

A process for the nitration of conjugated alkenes of formula (I) wherein R, R1, R2, R3 and R4 have the meanings reported in the description, which allows to obtain the corresponding β-nitro-alkenes, characterised in that the nitrating agent is a mixture of an inorganic nitrite and iodine in the presence of an oxidising agent is described.

16 Claims, No Drawings

PROCESS FOR THE PREPARATION OF NITROALKENES

This application is a continuation of application Ser. No. 10/311,319, now abandoned, which is a 371 of PCT/EP01/06902, filed Jun. 19, 2001.

The present invention relates to a process for the preparation of nitroalkenes and, more particularly, it relates to a process for the preparation of conjugated β-nitroalkenes by reaction of a conjugated alkene with a nitrite in the presence of iodine and of an oxidising agent. Conjugated β-nitroalkenes are widely used synthetic intermediates because they can be easily converted into a variety of different compounds. For example, we can cite β-nitrostyrene, useful intermediate for the preparation of several phenylethylamines and fungicides (Chemical Abstracts, vol. 118, no. 38576k), 2-nitro-dihydronaphthalenes, key intermediates for the synthesis of 2-amino-tetrahydronaphthalenes (Debasis Ghosh et al., Synthesis, 1996, pages 195–197) and 8-fluoro-3-nitro-2H-chromene-5-carboxylic acid amide, an intermediate for the preparation of (R)-3-dicyclobutylamino-8-fluoro-chroman-5-carboxylic acid amide, a compound useful in the treatment of disorders of the central nervous system (WO 98/46586-Astra Aktiebolag).

The nitration of alkenes with nitrites and iodine is known in the literature [Hassner et al., J. Org. Chem., 1969, 34(9), pages 2628–2632].

The method foresees the use of a mixture of silver nitrite and iodine as nitrating agent. After the paper of Hassner et al., some papers were published with the attempt of improving the nitration conditions.

Wing-Wah Sy et al. [Tetr. Lett., 1985, 26(9), pages 1193–1196] describe the nitration of substituted alkenes with silver nitrite and iodine, the only difference from Hassner et al. being the use of a higher molar amount of silver nitrite, which is then equimolar with respect to the iodine.

Jew et al. [Chemistry Letters, 1986, pages 1747–1748] replace silver nitrite with sodium nitrite and use 2 moles of iodine and 4 moles of nitrite per mole of styrene, respectively.

In the already cited paper published by Debasis Ghosh et al. potassium nitrite is used in the presence of a phase transfer catalyst and by treating with ultrasounds in order to increase the solubility of the nitrite ion. Different amounts of iodine were evaluated to optimise the yield and the reported general method foresees the use of 2.6 moles of nitrite and 2.75 moles of iodine per mole of alkene, respectively.

Then it is evident that the methods for the nitration of alkenes described in the literature show the relevant drawback of using high amounts of iodine which remarkably decrease the reaction productivity because of the high molecular weight of iodine, make the subsequent treatment with bisulphites, for transforming all the iodine in excess into iodides at the end of the reaction, particularly cumbersome and suffer from the problem of the removal of iodides from the waste waters.

We have now found that the amount of iodine to be used for the nitration of conjugated alkenes can be significantly decreased by adding an oxidazing agent to the reaction mixture containing the alkene, the nitrite and iodine.

Therefore, object of the present invention is a process for the nitration of conjugated alkenes of formula

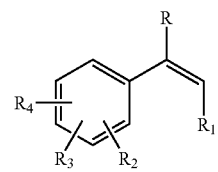

(I)

wherein

R is a hydrogen atom, an optionally substituted phenyl, a linear or branched $C_1$–$C_4$ alkyl; $R_1$ is a hydrogen atom or a linear or branched $C_1$–$C_4$ alkyl, optionally substituted by an OH or $C_1$–$C_4$ alkoxy group; $R_2$, $R_3$ and $R_4$, the same or different, are selected among hydrogen and halogen atoms, linear or branched $C_1$–$C_4$ alkyl or alkoxy groups, carboxylic groups, aminocarbonyl groups, alkyloxycarbonyl, alkylcarbonyl, mono- or di-alkylaminocarbonyl, alkylcarbonylamino and alkylcarbonyloxy groups having from 1 to 4 carbon atoms in the alkyl moiety; or two of $R_2$, $R_3$ and $R_4$, in ortho between them, form a methylendioxy group; or $R_1$ together with $R_2$ forms a cyclic system with 5–7 terms condensed with the aromatic ring and optionally containing an oxygen atom; or $R_1$ together with R forms a cyclic system with 5–7 terms;

which allows to obtain β-nitro-alkenes of formula

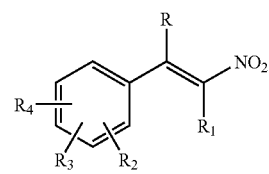

(II)

wherein R, $R_1$, $R_2$, $R_3$ and $R_4$ have the already reported meanings;

characterised in that the nitrating agent is a mixture of an inorganic nitrite and iodine in the presence of an oxidising agent.

The nitration process object of the present invention allows to obtain β-nitroalkenes under mild conditions with good yields.

In the present context, unless otherwise specified, linear or branched $C_1$–$C_4$ alkyl means an alkyl selected among methyl, ethyl, n-propyl, isopropyl, n-butyl, sec-butyl, isobutyl and t-butyl; linear or branched $C_1$–$C_4$ alkoxy means a group selected among methoxy, ethoxy, n-propoxy, isopropoxy, n-butoxy, sec-butoxy, isobutoxy and t-butoxy, halogen means fluorine, chlorine, bromine and iodine.

Substituted phenyl means a phenyl substituted by one or more substituents selected among the meanings of $R_2$, $R_3$ and $R_4$.

It is evident to the man skilled in the art that the substituents on the aromatic ring should be compatible with the used reaction conditions.

The compounds of formula I used in the nitration process object of the present invention are known.

Preferred examples of the compounds of formula I are styrenes optionally substituted on the aromatic ring by from 1 to 3 methoxy groups or by a methylenedioxy group, dihydronaphthalenes optionally substituted by methoxy, methyl, ethyl, fluoro, chloro, bromo, iodo, carboxy, methoxycarbonyl groups or by a methylenedioxy group or benzopyranes optionally substituted by methoxy, methyl, ethyl, fluoro, chloro, bromo, iodo, carboxy, methoxycarbonyl, aminocarbonyl or methylaminocarbonyl groups.

Particularly preferred are the nitration of the compounds of formula

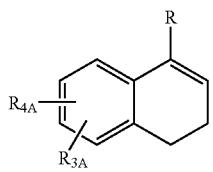

(I-A)

wherein $R_{3A}$ and $R_{4A}$, the same or different, are hydrogen atoms, methoxy, methyl, ethyl, fluoro, chloro, bromo, iodo, carboxy, methoxycarbonyl groups or, together, form a methylenedioxy group; R has the already reported meanings;

and the nitration of the compounds of formula

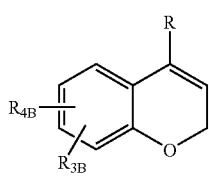

(I-B)

wherein $R_{3B}$ and $R_{4B}$, the same or different, are hydrogen atoms, methoxy, methyl, ethyl, fluoro, chloro, bromo, iodo, carboxy, methoxycarbonyl, aminocarbonyl or methylaminocarbonyl groups; R has the already reported meanings, to obtain the corresponding nitroderivatives of formula

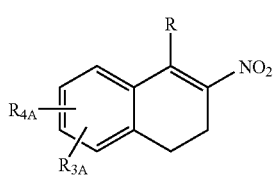

(II-A)

and of formula

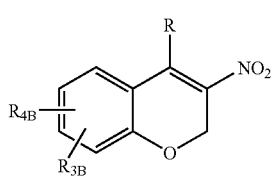

(II-B)

wherein R, $R_{3A}$, $R_{3B}$, $R_{4A}$ and $R_{4B}$ have the already reported meanings.

Examples of inorganic nitrites which can be used in the process object of the present invention are silver nitrite, sodium nitrite and potassium nitrite.

Preferably sodium nitrite is used.

The amount of nitrite is in excess with respect to the compound of formula I, generally not lower than 2 moles per mole of compound to be nitrated.

Preferably an amount of nitrite from 2 and 4 moles per mole of compound of formula I is used.

The most characterising feature of the present process is represented by the amount of iodine which is used.

In fact, the presence of an oxidising agent allows to significantly decrease the amount of iodine up to an amount generally equal or lower than 1 mole per mole of compound of formula I, preferably from 0.1 and 0.8 moles per mole of substrate to be nitrated.

As already underlined, the remarkable decrease of the amount of iodine necessary to carry out the nitration gives to the process object of the present invention the advantages related to the increased productivity and to the higher simplicity of the work-up of the reaction mixture. This is mainly in the final treatment to remove the iodine still present, which is generally carried out with bisulphite, but which can be also avoided in the process object of the present invention.

The advantages of the process object of the present invention are particularly evident by comparing the nitration reported in example 2 and the nitration carried out according to the prior art on the same substrate, as reported in the already cited WO 98/46586 (see in particular the example on page 12).

In fact, by working according to the method object of the present invention the nitroderivative is obtained with a practically triplicate yield.

Generally, the oxidation agent is slowly added, usually in 3–4 hours, to the reaction mixture containing the nitrite, iodine and the compound of formula I.

A hypothesis on the role of the oxidant is that of oxidising the iodides formed in the reaction mixture according to the following scheme $$AlkH + NaNO_2 + I_2 \rightarrow AlkNO_2 + HI + NaI$$

wherein AlkH represents the compound of formula I, so forming an amount of iodine which is sufficient to go on with the nitration reaction.

A further advantage is represented by the fact that, by using an oxidising agent, the iodine can also be prepared in situ by oxidation of iodides. Iodides which can be used for such purposes are generally alkali metal iodides, preferably potassium iodide.

Specific examples of oxidising agents which can be used in the process object of the present invention are peracids such as peracetic acid and m-chloroperbenzoic acid, hydrogen peroxide and inorganic nitrites, optionally in admixture each other.

It is evident that when an inorganic nitrite is used as oxidant agent, the same inorganic nitrite which is present in the nitrating mixture will be preferably used.

The oxidising agent must be used in an acid environment, preferably at a pH lower than 5.

Then, depending on the selected oxidant, it could be necessary also the addition of an acidifying agent to bring the pH up to the desired value.

Then, when peracids such as peracetic acid which is not sufficiently acid are used, it will be suitable to use the oxidant in solution with an acid solvent, preferably acetic acid. In a similar way, when hydrogen peroxide or an inorganic nitrite are used as oxidising agent, acetic acid will be preferably used.

The use of mixture of peracetic acid, hydrogen peroxide, acetic acid and water, already available on the market (Oxistrong®-Ausimont) is particularly advantageous.

It is evident that the amount of oxidant will be in relation to the used amount of iodine, preferably in slight excess. When the iodides are used to form iodine directly in the reaction medium, a higher amount of oxidant will be needed to allow the initial oxidation of the iodides. The process object of the present invention is carried out in the presence of a suitable organic solvent which is selected in relation to the solubility of the compound of formula I but which is not a critical parameter for the achievement of the process.

Examples of suitable solvents are esters such as ethyl acetate, isopropyl acetate and isobutyl acetate, aromatic hydrocarbons such as toluene and xylene, chlorinated hydrocarbons such as methylene chloride and 1,2-dichloropropane and ethers such as tert-butyl methyl ether.

When the reaction mixture contains water, the addition of a phase transfer catalyst can be useful.

Also the temperature is not a critical parameter. Preferably temperatures from 20° C. to 70° C. are used. A still more preferred temperature range is from 40° C. to 50° C.

A preferred embodiment of the process-object of the present invention is the following.

Iodine and then, slowly, a solution of the oxidising agent are added to a mixture of the alkene of formula I and of sodium nitrite in a suitable organic solvent. At the end of the addition and at the completion of the reaction, an aqueous solution of sodium metabisulphite is optionally added up to decoloration of the iodine and the compound of formula II is separated according to usual techniques.

In order to better illustrate the present invention the following examples are now given.

EXAMPLE 1

Preparation of 2-nitro-3,4-dihydronaphthalene

Into a three-necks flask equipped with a reflux condenser and a mechanic stirrer, at room temperature and under inert gas, 1,2-dihydronaphthalene (3.9 g; 30 mmoles), sodium nitrite (6.2 g; 90 mmoles) and isopropyl acetate (40 ml) were charged. The mixture was kept under stirring and heated at 50° C. Iodine (3:8 g; 15 mmoles) and then, through a rubber separator, a solution of peracetic acid in acetic acid (8.5 ml—solution 39% w/w) were added in 4 hours. At the end of the addition, the mixture was kept under stirring for further 30 minutes, cooled to 20° C., then a freshly prepared 10% sodium metabisulphite solution was slowly (15 minutes) added up to decoloration of iodine (about 30 ml). The phases were separated and the aqueous phase was washed with isopropyl acetate (2×10 ml). The collected organic phases were washed with a saturated sodium chloride aqueous solution (10 ml). After separation of the phases, the organic phase was dried on sodium sulphate, filtered and the solvent was removed under reduced pressure obtaining crude 2-nitro-3,4dihydronaphthalene (4.7 g; 73% yield) as a brown oil.

$M^+=175$

EXAMPLE 2

Preparation of 8-fluoro-3-nitro-2H-chromene-5-carboxylic acid amide

Into a reactor, equipped with a reflux condenser and under inert gas, 8-fluoro-2H-chromene-5-carboxylic acid amide (4.94 g; 25.6 mmoles), sodium nitrite (4.4 g; 64 mmoles) and isopropyl acetate (40 ml) were charged. The mixture was kept under mechanic stirring and heated at 50° C. In one portion iodine (1.9 g; 7.5 mmoles) and then, in 3 hours, Oxistrong 15® (6 ml) were added. At the end of the addition the reaction mixture was kept under stirring for 1 hour and cooled to 20° C. After addition of water (30 ml), the mixture was further cooled at 5° C. for 1 hour. The solid was filtered and washed with isopropyl acetate (3×10 ml), pre-cooled at 0° C., and with water (2×10 ml). After drying in oven under vacuum at 50° C. overnight, 8-fluoro-3-nitro-2H-chromene-5-carboxylic acid amide (4.7 g; HPLC titre 90%; 70% yield) was obtained. The mother liquors of the reaction were treated with a 15% solution of sodium metabisulphite (20 ml) up to decoloration. The phases were separated, the organic phase was dried and the organic solvent was removed under reduced pressure obtaining a solid (0.8 g) containing 49% of 8-fluoro-3-nitro-2H-chromene-5-carboxylic acid amide. Overall yield: 76.4%.

EXAMPLE 3

Preparation of 8-fluoro-3-nitro-2H-chromene-5-carboxylic acid amide

Into a reactor, equipped with a mechanic stirrer and a reflux condenser, 8-fluoro-2H-chromene-5-carboxylic acid amide (3.1 g; 15 mmoles), sodium nitrite (3.1 g; 45 mmoles) and toluene (30 ml) were charged at room temperature and under inert gas. The mixture was heated under stirring at 50° C., then iodine (1.9 g; 7.5 mmoles) and, slowly in 4 hours, Oxistrong 15® (3.7 ml) were added. At the end of the addition the reaction mixture was kept under stirring for a further hour, then cooled to 0° C. A 20% solution of sodium metabisulphite (about 15 ml) was added and the mixture was kept under stirring for 1 hour. After filtration the solid was washed with water (2×10 ml) and with toluene (10 ml) and dried in oven under vacuum at 50° C. overnight obtaining 8-fluoro-3-nitro-2H-chromene-5-carboxylic acid amide (3.4 g; titre 78%; 74% yield).

EXAMPLE 4

Preparation of 8-fluoro-3-nitro-2H-chromene-5-carboxylic acid methyl ester

Into a reactor, equipped with mechanic stirrer and reflux condenser, 8-fluoro-2H-chromene-5-carboxylic acid methyl ester (6.6 g; 30 mmoles), sodium nitrite (6.2 g; 90 mmoles) and ethyl acetate (60 ml) were added at room temperature and under inert gas. The mixture was heated under stirring at 50° C., then iodine (2:6 g; 10 mmoles) and, slowly in 4 hours, Oxistrong 15® (7.4 ml) were added. At the end of the addition the reaction mixture was kept under stirring for a further hour, then cooled at 0° C. A 20% solution of sodium metabisulphite (about 25 ml) was added and the mixture was kept under stirring for 1 hour. After filtration the solid was washed with water (2×10 ml). The mother liquors were separated and, the previously filtered solid was added to the organic phase. The solvent was removed under reduced pressure and the semisolid residue was taken up with methanol (about 10 ml) and kept under stirring at 0° C. for 1 hour. After filtration and wash of the panel with methanol pre-cooled at 0° C. (3 ml), the resultant solid was dried in oven under vacuum at 40° C. overnight obtaining 8-fluoro-3-nitro-2H-chromene-5-carboxylic acid methyl ester (4.6 g; titre 92%; 55% yield). The mother liquors were evaporated to dryness obtaining an oil (2.7 g) containing 55% of 8-fluoro-3-nitro-2H-chromene-5-arboxylic acid methyl ester. Overall yield 75%.

EXAMPLE 5

Preparation of 8-fluoro-3-nitro-2H-chromene-5-carboxylic acid amide

Into a reactor, equipped with a mechanic stirrer and a reflux condenser, 8-fluoro-2H-chromene-5-carboxylic acid amide (2 g; 10 mmoles), sodium nitrite (1.4 g; 20 mmoles), potassium iodide (0.33 g; 2 mmoles) and ethyl acetate (20 ml) were charged at room temperature and under inert gas. The mixture was heated at 40° C., then Oxistrong 15® (4 ml) was added in 4 hours. At the end of the addition the reaction mixture was kept under stirring for 1.5 hours, then cooled at 20° C. and diluted with ethyl acetate up to complete dissolution (about 150 ml). After washing with a 20% sodium metabisulphite solution, the phases were separated. The organic phase was washed with a saturated sodium chloride solution, dried and the solvent was removed under reduced pressure, obtaining 8-fluoro-3-nitro-2H-chromene-5-carboxylic acid amide (1.8 g; titre 88%; 66% yield).

EXAMPLE 6

Preparation of 8-fluoro-3-nitro-2-H-chromene-5-carboxylic acid amide

Into a reactor, equipped with a mechanic stirrer and a reflux condenser, 8-fluoro-2H-chromene-5-carboxylic acid amide (120 g;0.609 moles), sodium nitrite (96.6 g; 1.4 moles), iodine (31.2 g; 0.123 moles) and ethyl acetate (720 ml) were charged at room temperature and under inert gas. The mixture was heated under stirring at 40° C., then Oxistrong 15® (173.4 g) was added in 4 hours. At the end of the addition the reaction mixture was kept under stirring for 1 hour, then cooled at 20° C. Water (480 ml) was added and the mixture was kept under stirring for 1 hour. After filtration and wash of the panel with isopropyl acetate pre-cooled at 0° C. (2×120 ml) and then with water (150 ml), the solid was dried in oven under vacuum at 50° C. overnight obtaining 8-fluoro-3-nitro-2H-chromene-5-carboxylic acid amide (112.7 g; titre 91%; 70% yield).

The invention claimed is:

1. A process comprising nitration of conjugated alkenes with a nitrating agent to obtain β-nitro-alkenes, wherein the conjugated alkenes are of formula

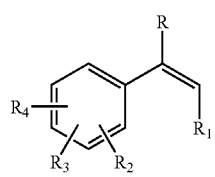

(I)

wherein

R is a hydrogen atom, an optionally substituted phenyl, a linear or branched $C_1$–$C_4$ alkyl; $R_1$ is a hydrogen atom or a linear or branched $C_1$–$C_4$ alkyl, optionally substituted by an OH or $C_1$–$C_4$ alkoxy group; $R_2$, $R_3$ and $R_4$, the same or different, are selected among hydrogen and halogen atoms, linear or branched $C_1$–$C_4$ alkyl or alkoxy groups, carboxylic groups, aminocarbonyl groups, alkyloxycarbonyl, alkylcarbonyl, mono- or di-alkylammocarbonyl, alkylcarbonylamino and alkylcarbonyloxy groups having from 1 to 4 carbon atoms in the alkyl moiety; or two of $R_2$, $R_3$ and $R_4$, adjacent to each other, form a methylendioxy group; or $R_1$ together with $R_2$ forms a cyclic system with 5–7 atoms condensed with the aromatic ring and optionally containing an oxygen atom; or $R_1$ together with R forms a cyclic system with 5–7 atoms;

the β-nitro-alkenes are of formula

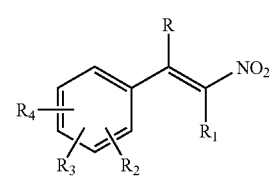

(II)

wherein R, $R_1$, $R_2$, $R_3$ and $R_4$ have the already reported meanings;

and wherein the nitrating agent is a mixture of an inorganic nitrite and iodine in the presence of an oxidizing agent selected from the group consisting of peracids, hydrogen peroxide, and mixtures thereof.

2. A process according to claim 1 wherein the iodine is in an amount from 0.1 to 0.8 moles per mole of the compound of formula I.

3. A process according to claim 1 wherein the inorganic nitrite is selected among silver nitrite, sodium nitrite and potassium nitrite.

4. A process according to claim 3 wherein the inorganic nitrite is sodium nitrite.

5. A process according to claim 1 wherein the inorganic nitrite is in an amount from 2 to 4 moles per mole of the compound of formula I.

6. A process according to claim 1 wherein the oxidising agent is a mixture of peracetic acid, hydrogen peroxide and water.

7. A process according to claim 1 wherein the iodine is formed in situ from alkaline iodides.

8. A process according to claim 1 wherein the nitration is carried out at a temperature of from 40° C. to 50° C.

9. A process according to claim 1, wherein the conjugated alkenes are styrenes, optionally substituted on the aromatic ring by from 1 to 3 methoxy groups or by a methylenedioxy group.

10. A process according to claim 1, wherein the conjugated alkenes are dihydronaphthalenes, optionally substituted by methoxy, methyl, ethyl, fluoro, chloro, bromo, iodo, carboxy, methoxycarbonyl groups or by a methylenedioxy group.

11. A process according to claim 10, wherein the dihydronapthalenes are of formula

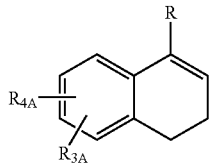

(I-A)

wherein $R_{3A}$ and $R_{4A}$, the same or different, are hydrogen atoms, methoxy, methyl, ethyl, fluoro, chloro, bromo, iodo, carboxy, methoxycarbonyl groups or, together, form a methylenedioxy group;

R is a hydrogen atom, an optionally substituted phenyl, or a linear or branched $C_1$–$C_4$ alkyl.

12. A process according to claim 1, wherein the conjugated alkenes are benzopyranes optionally substituted by methoxy, methyl, ethyl, fluoro, chloro, bromo, iodo, carboxy, methoxycarbonyl, aminocarbonyl or methylaminocarbonyl groups.

13. A process according to claim 12 wherein the benzopyranes are of formula

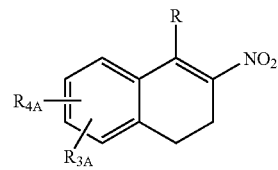

(II-A)

wherein $R_{3B}$ and $R_{4B}$, the same or different, are hydrogen atoms, methoxy, methyl, ethyl, fluoro, chloro, bromo, iodo, carboxy, methoxycarbonyl, aminocarbonyl or methylaminocarbonyl groups;

R is a hydrogen atom, an optionally substituted phenyl, or a linear or branched $C_1$–$C_4$ alkyl.

14. A process according to claim 12 wherein the benzopyrane is the compound 8-fluoro-2H-chromene-5-carboxylic acid amide.

15. A process according to claim 1, which is carried out under acid conditions.

16. A process according to claim 15, wherein the acid conditions are a pH lower than 5.

* * * * *